(12) United States Patent
Alghamdi

(10) Patent No.: US 9,487,540 B2
(45) Date of Patent: *Nov. 8, 2016

(54) COMPOUND FOR INHIBITING THE GROWTH AND PROLIFERATION OF HUMAN LIVER CANCER CELLS AND METHOD FOR SYNTHESIZING IT

(71) Applicant: Zainab Saeed Alghamdi, Dhahran (SA)

(72) Inventor: Zainab Saeed Alghamdi, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 14/668,837

(22) Filed: Mar. 25, 2015

(65) Prior Publication Data
US 2016/0280717 A1   Sep. 29, 2016

(51) Int. Cl.
*C07D 495/04*   (2006.01)
(52) U.S. Cl.
CPC .................................. *C07D 495/04* (2013.01)
(58) Field of Classification Search
CPC .................................................. C07D 495/04
See application file for complete search history.

(56) References Cited

U.S. PATENT DOCUMENTS

2009/0143411 A1\* 6/2009 Ward .................. C07D 333/38
514/258.1

\* cited by examiner

*Primary Examiner* — Sarah Pihonak
(74) *Attorney, Agent, or Firm* — Dennis H. Lambert

(57) ABSTRACT

The compound "2-((4-nitrophenyl)amino)-6,7,8,9-tetrahydro-3H-cyclohepta[4,5]thieno-[2,3-d]pyrimidin-4(5H)-one" and method of synthesizing it, wherein the compound is effective to inhibit the growth and proliferation of human liver cancer cells HepG2. The compound has an inhibitory concentration value ($IC_{50}$) of 0.7 μg, compared to reference medication Doxorubicin that has an ($IC_{50}$) value of 1.2 μg. It further surpasses that reference medication Doxorubicin at all tested concentraions. The method includes the steps of: preparing a first compound of cycloheptanone, ethylcyanoacetate, sulfur, ethanol and diethyl amine; preparing a second compound by heating of the first compound with excess of hydrazine hydrate in absolute ethanol as solvent; and preparing the effective compound of the invention by reaction of the second chemical compound with 4-nitrophenylisothiocyanate in dry dimethylformamide as solvent.

17 Claims, 15 Drawing Sheets

COMPOUND FOR INHIBITING THE GROWTH AND PROLIFERATION OF HUMAN LIVER CANCER CELLS AND METHOD FOR SYNTHESIZING IT

TECHNICAL FIELD

This invention relates to chemical compounds useful in the treatment of diseases, and particularly to a new compound for the treatment of human liver cancer and to a method for synthesizing the compound.

BACKGROUND ART

There are more than 200 types of cancer, each with different causes, symptoms and treatments. Cancer is among the leading causes of morbidity and mortality worldwide. There were approximately 14.1 million new cases of cancer and 8.2 million cancer related deaths in 2012, with incidence rates varying across the world.

Cancer is the second leading cause of death in the United States, exceeded only by heart disease. In the United States in 2014, nearly 586,000 people are expected to die of cancer and more than 1.66 million new cancer cases are expected to be diagnosed, but the cost of cancer extends beyond the number of lives lost and new diagnoses each year. Cancer survivors, as well as their family members, friends, and caregivers, may face physical, emotional, social, and spiritual challenges as a result of their cancer diagnosis and treatment. The financial costs of cancer also are overwhelming. According to the National Institutes of Health, cancer cost the United States an estimated $263.8 billion in medical costs and lost productivity in 2010.

Hepatocellular carcinoma is one of the most lethal human cancers because of its high incidence and its metastatic potential, and it is among the most resistant to treatment. It is the third leading cause of cancer-related deaths worldwide.

Substantial research has been conducted worldwide, with limited success, in an effort to find effective treatments and/or a cure for cancer. The examples below describe some of those efforts, although the article in *Molecules* by M. Ismail, et al relates to the treatment of Alzheimer's disease, and the article by M. Raghuprasad, et al in the *Asian Journal of Chemistry* and the article by B. V. Ashalatha, et al in the *European Journal of Medicinal Chemistry* both relate to antimicrobial activity.

In a research paper by Rafat Mohareb and Abdelgawad Fahmy, titled *Cytotoxicity of Novel 4,5,6,7-Tetrahydrobenzo[b]thiophene Derivatives and Their Uses As Anti-Leishmanial Agents*, published in the European Chemical Bulletin, 2013, 2(8), 545-553, the authors studied the cytotoxicity of 4,5,6,7-tetrahydrobenzo[b]thiophene derivatives in the treatment of breast adenocarcinoma, non-small-cell lung cancer, and central nervous system lymphoma (CNS lymphoma). The compounds proposed by Mohareb and Fahmy all have a thiophene ring attached to the cyclohexene ring. The chemical structure is depicted in FIG. 1.

In a paper by Dhilli Gorja, Shiva Kumar, K. Mukkanti, and Manojit Pal, titled *C—C(alkynylation) vs C—O (ether) Bond Formation Under Pd/C—Cu Catalysis; Synthesis and Pharmacological Evaluation of 4-Alkynylthieno[2,3-d]pyrimidines*, published in the Journal of Organic Chemistry 2011, 7, 338-345, the authors proposed alkynyl substituted thienopyrimidines, notably 6-ethynylthieno[3,2-d]- and 6-ethynylthieno[2,3-d]pyrimidin-4-aniline derivatives useful in the treatment of leukemia. The authors used a Pd/C-CuI-PPh$_3$ catalytic system to facilitate C—C bond formation between 4-chlorothieno[2,3-d]pyrimidines and terminal alkynes in methanol. A variety of 4-alkynylthieno[2,3-d]pyrimidines were prepared via alkynylation of 4-chlorothiene[2,3-d]pyrimidines. Such chemical structure is depicted in FIG. 2.

In an article titled *Synthesis and Biological Evaluation of Thiophene Derivatives As Acetylcholinesterase Inhibors*, published in Molecules 2012, 17, 7217-7231, Mohamed Ismail, Mona Kamel, Lamia Mohamed, Samar Faggal and Mai Galal proposed thiophene derivatives as acetylcholinesterase inhibitors useful in the treatment of Alzheimer's disease. The chemical structure is depicted in FIG. 3.

M. Raghuprasad, S. Mohan, B. Das and S. Srivastava published in the Asian Journal of Chemistry 2007; 19(5): 2813-7, a paper titled *Synthesis and Antimicrobial Activity of Some Thiadiazolo Thienopyrimidines*, in which thiadiazolo thienopyrimidin derivatives are attached with cyclohexene ring and the benzene ring is attached with methoxy group (—OCH$_3$), but do not have a carbonyl group (C=O) nor is a benzene ring attached with a nitro group (—NO$_2$). The biological objective in their paper was antimicrobial activity. The chemical structure is depicted in FIG. 4.

B. V. Ashalatha, B. Narayana, K. K Raj Vijaya and S. Kumari published in the European Journal of Medicinal Chemistry 2007, 42, 719-728, a paper titled *Synthesis of Some New Bioactive 3-Amino-2-mercabto-5,6,7,8-tetrahydro[1]benzothieno[2,3-d]pyrimidin-4-one Derivatives*, in which their compounds have thiadiazolo thienopyrimidin derivatives attached with cyclohexene ring. The compound is not attached with a cycloheptene ring. Their biological objective was antimicrobial, anti-inflammatory, anticonvulsant and neuropsychobehavioural effects. The chemical structure is depicted in FIG. 5.

V. Alagarsamy, U.S. Pathak, V. Rajasolomon, S. Meena, K. V. Ramseshu, and R. Rajesh published in the Indian Journal of Heterocyclic Chemistry 2004; 13; 347. 2004; 13; 347 an article titled *Anticancer, Antibacterial and Antifungal Activities Of Some 2-substituted(1,3,4)thiadiazolo(2,3-b)tetrahydrobenzo(b)thieno(3,2-e)pyrimidines*, wherein they synthesized (1,3,4) thiadiazole(2,3-b)tetrahydro-benzothieno[3,2-e]pyrimidines and then screened them for anticancer, antibacterial and antifungal activities. Their compounds have thiadiazolo thienopyrimidin derivatives attached with cyclohexene ring. The compound is not attached with cycloheptene ring. Their objectives are anticancer, antibacterial and antifungal. The chemical structure is depicted in FIG. 6.

Drugs have been developed that produce favorable results in some cancers that are more susceptible to treatment, but no really effective drug has been developed for the treatment of hepatocellular carcinoma. The compounds mentioned in the articles noted above have limited, if any, effectiveness in the treatment of liver cancer.

Accordingly, there is a need for a treatment that is more effective in reducing the growth and propagation of human liver cancer cells (HepG2).

SUMMARY OF THE INVENTION

Applicant has synthesized a new chemical compound for reducing the growth and propagation of human liver cancer cells (HepG2). The compound was tested on human liver cancer cells for effectiveness at various degrees of concentration.

The test results revealed that the new compound has a higher efficiency to inhibit the growth and proliferation of these cells as it has an inhibition concentration value (IC$_{50}$)

of 0.7 µg compared to the reference medication (Doxorubicin) that has an inhibition concentration value ($IC_{50}$) of 1.2 µg. Not only do the test results confirm the high efficiency of the compound of the invention but also the potential therapeutic benefit from using it.

The effective chemical compound of the invention is synthesized by:

1) first preparing a compound I (founding compound) in accordance with one of several methods, preferably according to Gewald, wherein compound I has the chemical formula "Ethyl 2-amino-5,6,7,8-tetrahydro-4H-cyclohepta[b]thiophene-3-carboxylate";
2) second, preparing a compound II in accordance with one of several available methods, preferably by heating of compound I with excess of hydrazine hydrate in absolute ethanol as solvent, wherein compound II has the chemical formula "2-Amino-5,6,7,8-tetrahydro-4H-cyclohepta[b]thiophene-3-carbohydrazide"; and
3) third, preparing the effective compound of the invention, compound III, by reacting compound II with 4-nitrophenylisothiocyanate in dry dimethylformamide (DMF) as solvent. wherein the compound of the invention has the chemical formula "2-((4-Nitrophenyl)amino)-6,7,8,9-tetrahydro-3H-cyclohepta[4,5]thieno[2,3-d]pyrimidin-4(5H)-one".

As shown in FIG. 19, the compound of the invention was prepared by a series of chemical reactions where 4-nitrophenylisothiocyanate was reacted with the 2-amino-3-carbohydrazide derivative (compound II). The latter (compound II) was prepared by the reaction of founding (compound I) with excess of hydrazine hydrate.

All compounds were characterized by using different spectrum means such as infrared, nuclear magnetic resonance for protons, nuclear magnetic resonance for carbons and finally mass spectrum.

The effectiveness of the compound of the invention, compound III, "2-((4-nitrophenyl)amino)-6,7,8,9-tetrahydro-3H-cyclohepta[4,5]thieno[2,3-d]pyrimidin-4(5H)-one", was tested on human liver cancer cells (HepG2) by using isolated-biopsy cells from males with an average age of about 15 years. The new compound was found to have a higher efficiency to inhibit the growth and proliferation of these cells as it has an inhibition concentration value ($IC_{50}$) of 0.7 µg which surpasses, at all tested concentrations, the reference medication (Doxorubicin) that has an inhibition concentration value ($IC_{50}$) of 1.2 µg.

As shown by applicant's discovery, the invention compound is medically effective as a new treatment for human liver cancer.

BRIEF DESCRIPTION OF THE DRAWINGS

The foregoing, as well as other objects and advantages of the invention, will become apparent from the following detailed description when taken in conjunction with the accompanying drawings, wherein like reference characters designate like parts throughout the several views, and wherein.

DETAILED DESCRIPTION OF THE BEST MODES OF CARRYING OUT THE INVENTION

Figure 19:
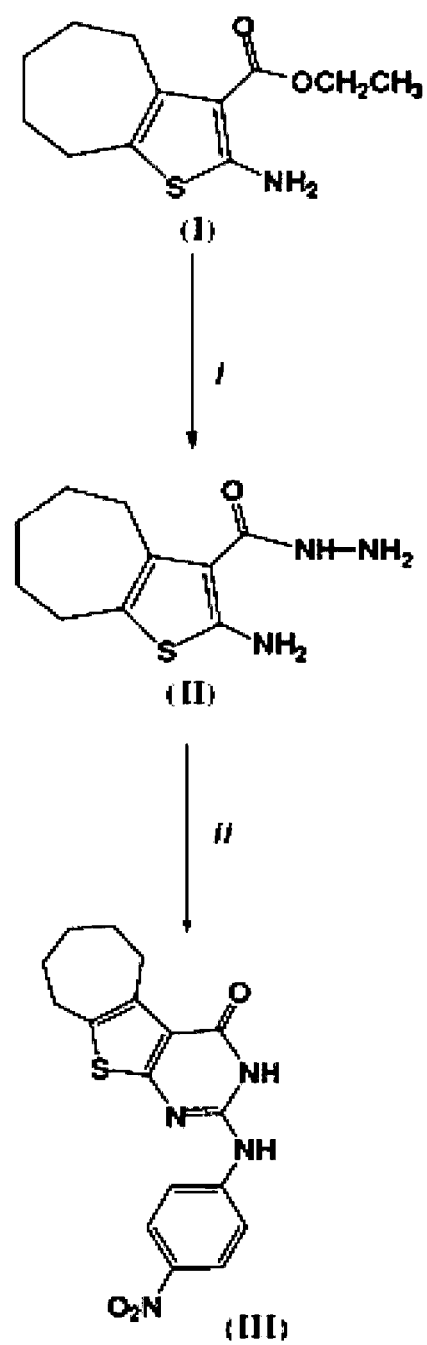
FIG. 19 shows the series of chemical reactions that produce the chemical compound of the invention (compound III).

The chemical compound of the invention, "2-((4-Nitrophenyl)amino)-6,7,8,9-tetrahydro-3H-cyclohepta[4,5]thieno[2,3-d]pyrimidin-4(5H)-one" (compound III) was prepared by a series of chemical reactions where 4-nitrophenylisothiocyanate was reacted with the "2-Amino-5,6,7,8-tetrahydro-4H-cyclohepta[b]thiophene-3-carbohydrazide" (compound II). The latter (compound II) was prepared by the reaction of founding compound "Ethyl-2-amino-5,6,7,8-tetrahydro-4H-cyclohepta[b]thiophene-3-carboxylate" (compound I) with excess of hydrazine hydrate as shown in FIG. 19.

Compound I:

The founding compound, compound I, "Ethyl-2-amino-5,6,7,8-tetrahydro-4H-cyclohepta[b]thiophene-3-carboxylate", can be prepared by a number of known conventional ways, but in the preferred method according to the present invention was prepared according to Gewald (Gewald, K., E. Schinke, and H. Böttcher, *Heterocyclen aus CH-aciden Nitrilen, VIII. 2-Amino-thiophene aus methylenaktiven Nitrilen, Carbonylverbindungen und Schwefel. Chemische Berichte*, 1966, 99(1): p. 94-100). Gewald devised the most facile and promising set of synthetic reactions leading to 2-aminothiophene with a carboxylate group in position 3.

The second version of the Gewald reactions consists of a one-pot procedure that is extensively used for this synthesis. The convenient technique includes the condensation of cycloheptanone, ethyl cyanoacetate and a sulfur element in ethanol with the presence of amine as diethyl amine for 24 hours at room temperature.

Figure 1:
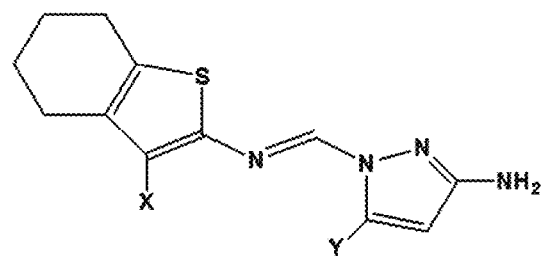
FIG. 1 shows the chemical structure of the prior art compounds proposed by Mohareb and Fahmy.
Figure 2:
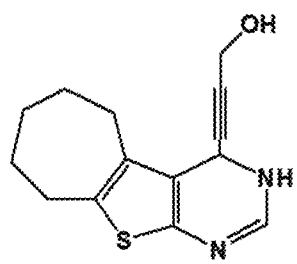
FIG. 2 shows the chemical structure of the prior art compound proposed by Gorja, et al.
Figure 3:
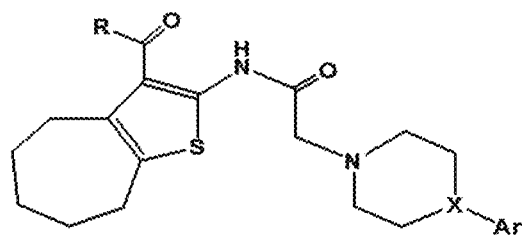
FIG. 3 shows the chemical structure of the prior art compound proposed by Ismail, et al.
Figure 4:
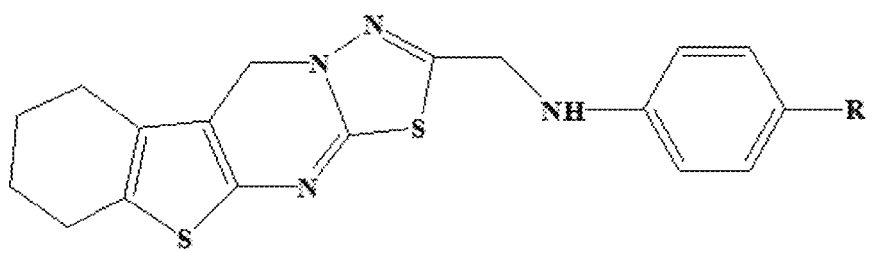
FIG. 4 shows the chemical structure of the prior art compound proposed by Raghuprasad, et al.
Figure 5:
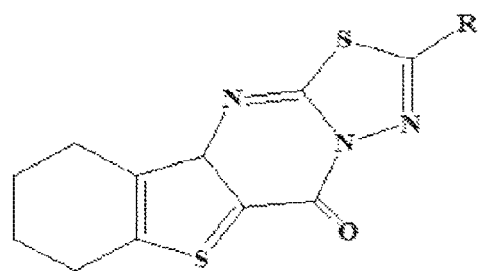
FIG. 5 shows the chemical structure of the prior art compound proposed by Ashalatha, et al.
Figure 6:
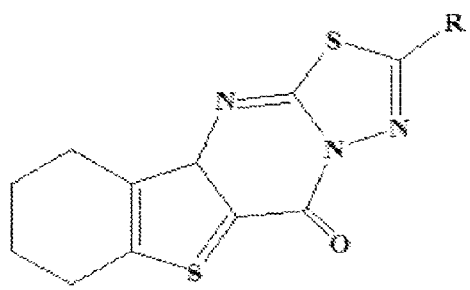
FIG. 6 shows the chemical structure of the prior art compound proposed by Alagarsamy, et al.
Figure 7:
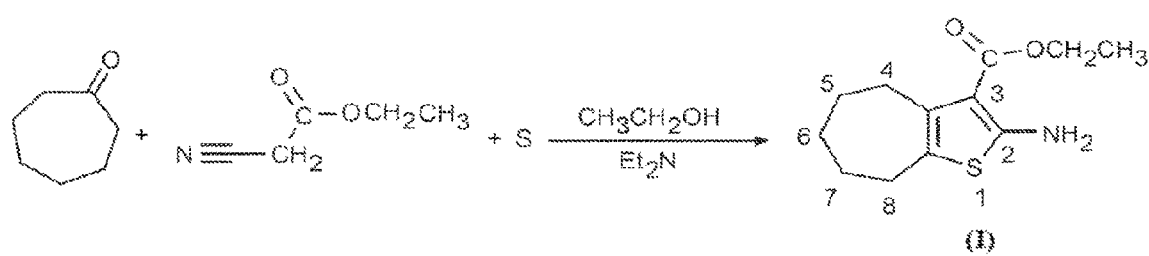
FIG. 7 shows the chemical reactions that produce the founding compound (compound I) in accordance with the teachings of Gewald, and that is used in synthesizing the compound of the invention.
Figure 8:
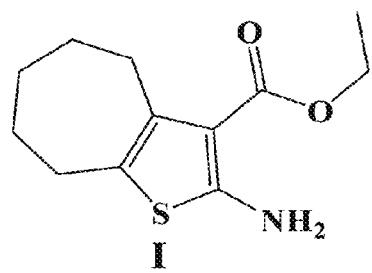
FIG. 8 shows the chemical structure of compound I.

The structure of compound (I), shown in FIG. 8, was assigned on the basis of the infrared spectra (IR), proton nuclear magnetic resonance spectrum ($^1$H-NMR), carbon nuclear magnetic resonance spectrum ($^{13}$C-NMR), X-ray spectrum, and mass spectrum (MS) spectral data, as shown in FIGS. 9-13, respectively.

In the preparation of compound (I) according to the preferred method, cycloheptanone (5.60 g, 0.05 mmol), ethylcyanoacetate (5.65 g, 0.05 mmol), sulfur (1.67 g) and ethanol (10 ml) were mixed and stirred together. To this well stirred mixture diethyl amine was added drop wise (10 ml) until the sulfur dissolved and the mixture was stirred on cold for overnight. The reaction mixture was treated with crushed ice (60 ml), and the solid product was filtered off, dried and recrystallized by petroleum ether (60-80%).

Figure 9:
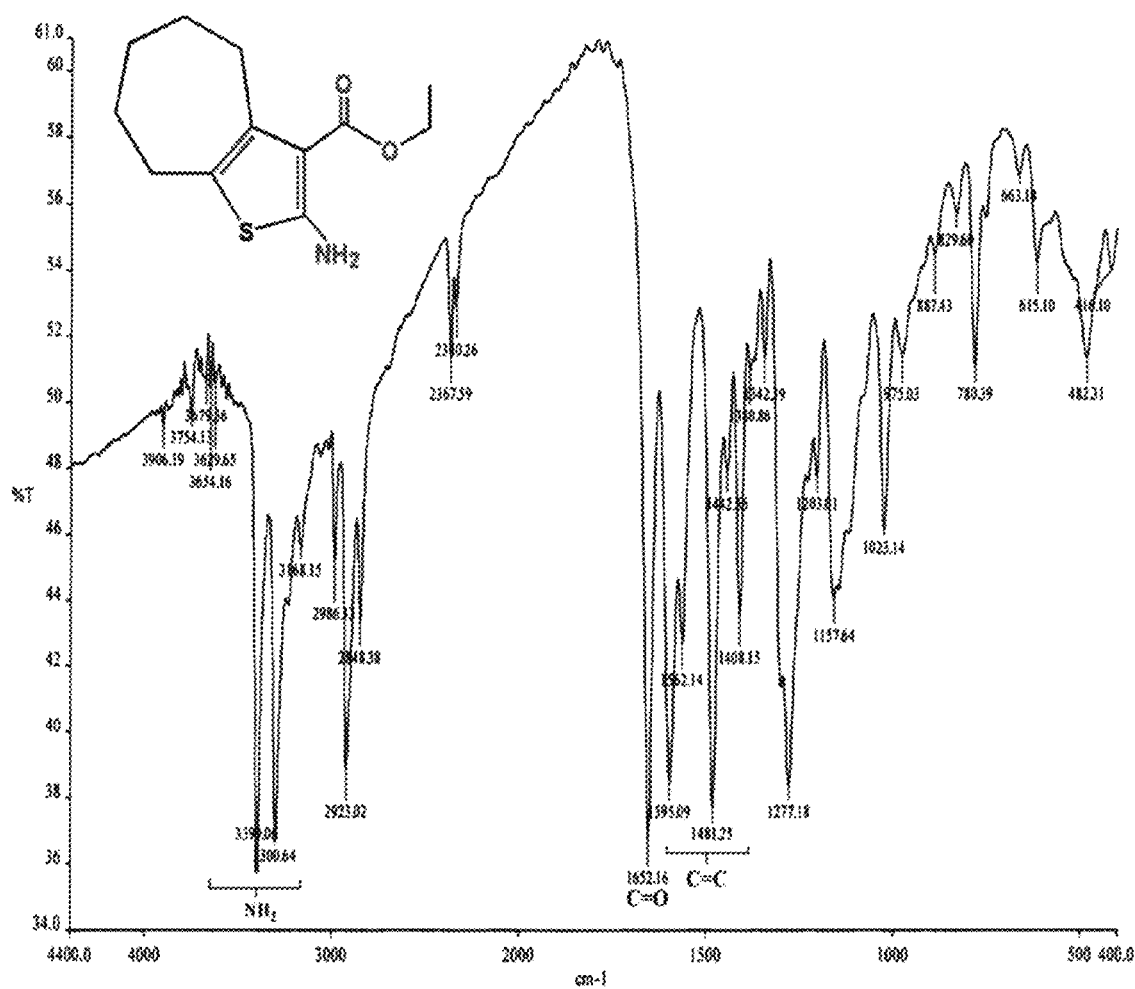
FIG. 9 depicts the Infrared spectra of compound I.

The infrared spectra (IR) of compound (I), see FIG. 9, showed absorption peaks at 3399.06, 3300.64 cm$^{-1}$ (NH$_2$), 1652.16 cm$^{-1}$ (C=O ester), 1595.09, and 1562.14 cm$^{-1}$ (C=C).

Figure 10:
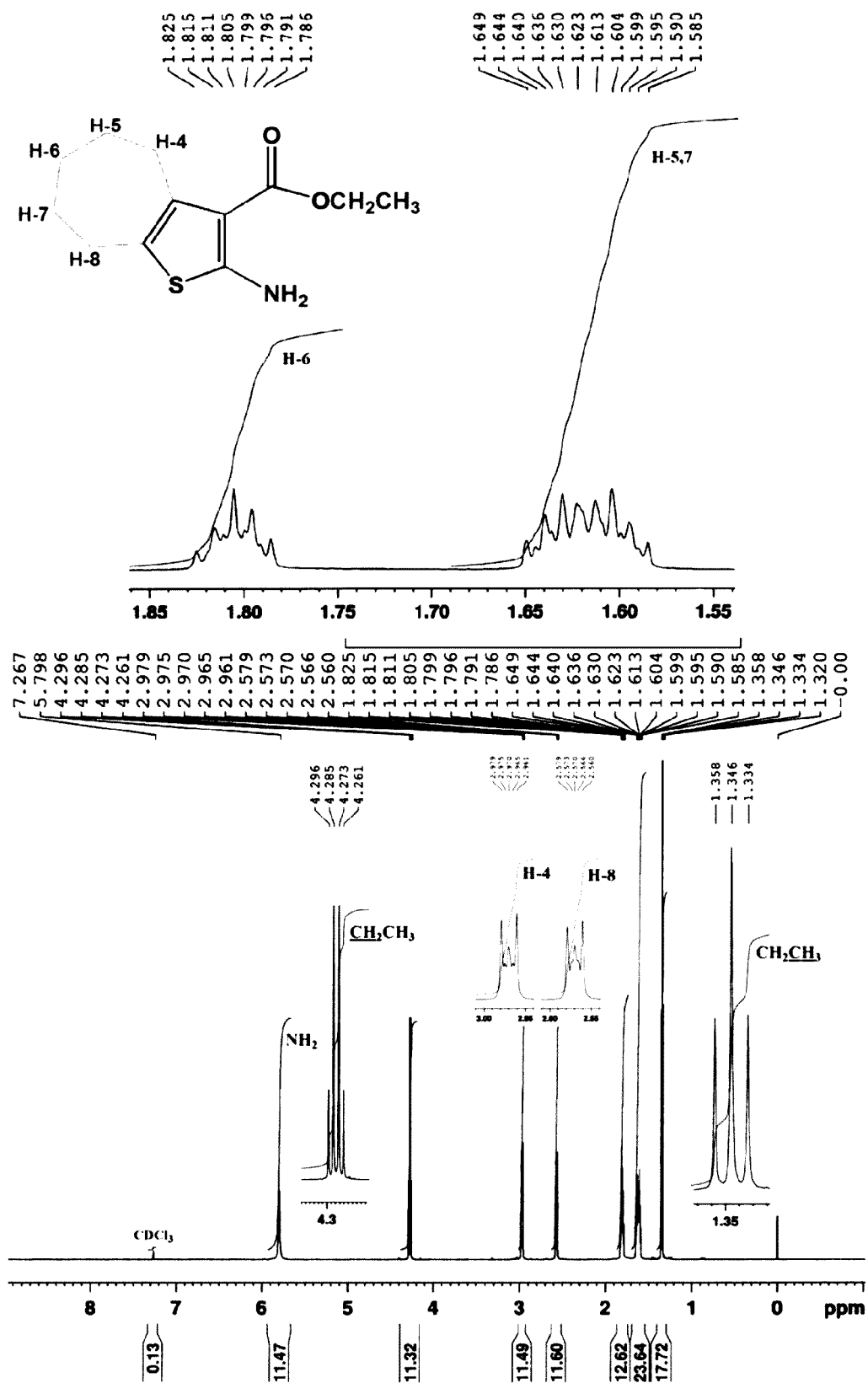
FIG. 10 depicts the nuclear magnetic resonance spectrum of the protons in compound I.

The proton nuclear magnetic resonance spectra ($^1$H-NMR) of compound (I), see FIG. 10, showed a triplet at δ 1.35 ppm (3H, $^3$J=7.2 Hz) corresponding to the three hydrogens of CH$_3$ ester, a multiplet at δ 1.59-1.65 ppm (4H, H-5,7), a multiplet at δ 1.81 ppm (2H, H-6), a triplet at δ 2.57 ppm (2H, $^3$J=5.4 Hz, H-8), a triplet at δ 2.84 ppm (2H, $^3$J=5.4 Hz, H-4) corresponding to the methylene groups protons in the cycloheptene moiety and quartet at δ 4.28 ppm corresponding to the two hydrogens of CH$_2$ ester, while the NH$_2$ protons appeared as a single at δ 5.80 ppm (2H).

Figure 11:
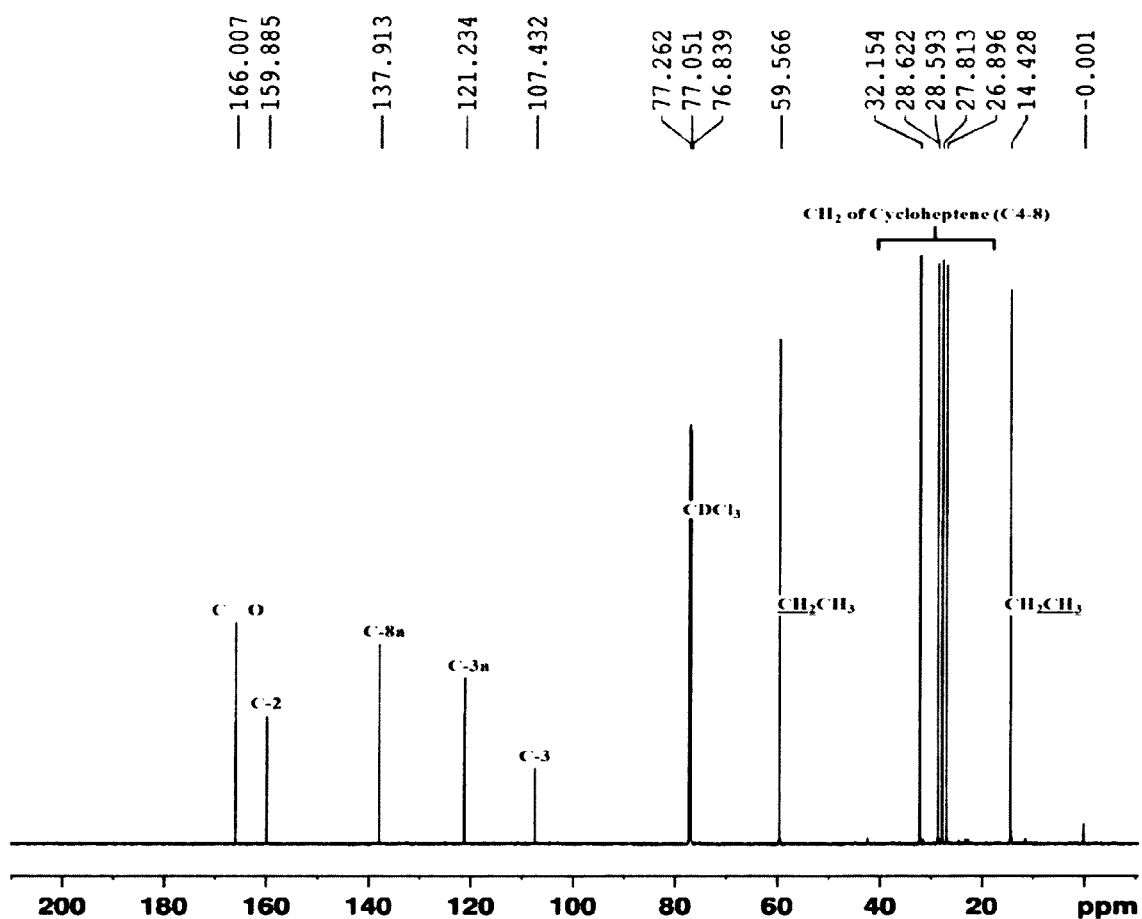
FIG. 11 depicts the nuclear magnetic resonance spectrum of the carbons in compound I.

The carbon nuclear magnetic resonance spectra ($^{13}$C-NMR) of compound (I, see FIG. 11, showed CH$_3$-ester at δ 14.43 ppm, cycloheptene as five peaks at δ 26.90, 27.82, 28.60, 28.62, and 32.15 ppm (C4-8), CH$_2$—ester at δ 59.57 ppm and thiophene ring showed as four peaks at δ 107.43 ppm (C-3), 121.23 ppm (C-3a), 137.91 ppm (C-8a), 159.89 ppm (C2), while carbonyl carbon appeared at δ 166.01 ppm.

Figure 12:
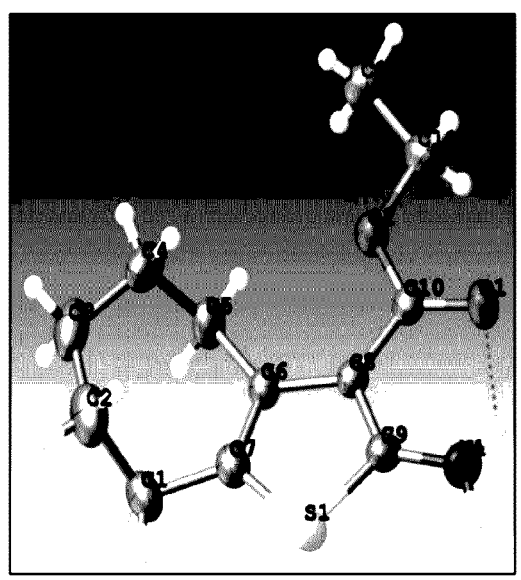
FIG. 12 depicts the X-ray spectrum of compound I.
Figure 13:
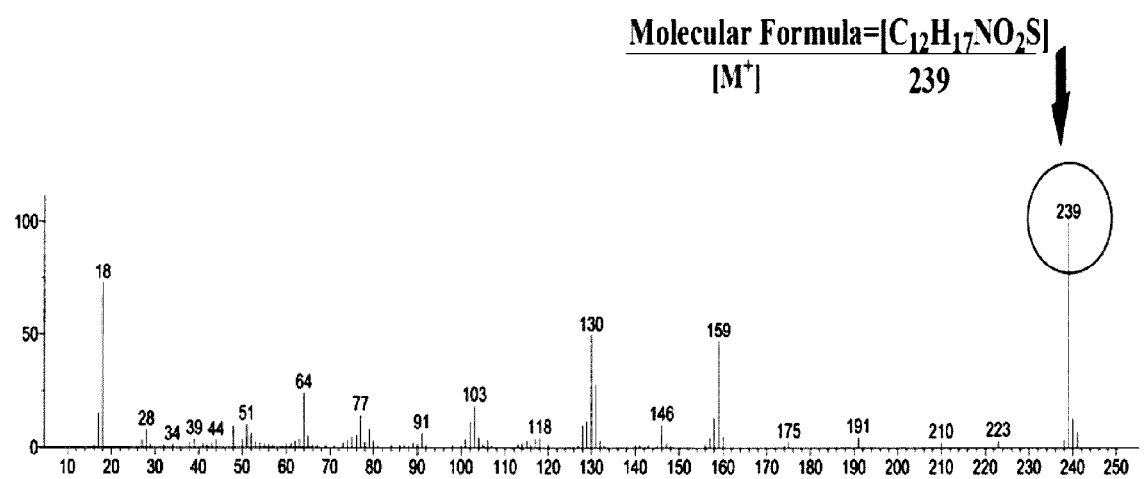
FIG. 13 depicts the mass spectrum of compound I.

As shown in FIG. 12, the X-ray for compound I conformed the structure.

The mass spectra (MS) for compound (I), see FIG. 12, showed the molecular ion peak at m/z 239 (99.9%) and the fragments, m/z (%): 239 (99.9) [M$^+$], 223 (3.2), 210 (2.5), 159 (47), 130 (49.8), 103 (18.6), 64 (24.2) and 18 (72.7).

Compound II:

Several methods (methods A, B and C) were used for the preparation of compound II (carboxylic acid hydrazide). These methods mainly react compound I (carboxylic acid ester) with hydrazine or hydrazine derivatives in ethanol. Compound II, "2-Amino-5,6,7,8-tetrahydro-4H-cyclohepta[b]thiophene-3-carbohydrazide" was prepared via prolonged heating of "2-Amino thiophene-3-carboxylate derivative" compound I with excess of hydrazine hydrate in absolute ethanol as solvent by the conventional methods (method A), by microwave (method B), and by ultrasonic sound (method C).

In accordance with method A, the conventional method, a mixture of compound I (0.24 g, 1 mmol) and excess of hydrazine hydrate (5 mmol) in absolute ethanol (20 ml, 99.9%) was refluxed for 18 hours. After cooling, the reaction mixture was treated with crushed ice (50 ml), and the solid product was filtered off, dried and recrystallized by hexane.

In accordance with method B, microwave irradiated method, a mixture of compound I (0.24 g, 1 mmol) and hydrazine hydrate (1 ml) and 2 drops of absolute ethanol was exposed to microwave and irradiated at 390 W for 30 minutes. After cooling, the reaction mixture was treated with crushed ice (20 ml), and the solid product was filtered off, dried and recrystallized by hexane.

In accordance with method C, the ultrasound irradiated method, compound I (0.24 g, 1 mmol) and excess of hydrazine hydrate (5 mmol) in absolute ethanol (10 ml) was irradiated by ultrasound for 4 hours. After cooling, the reaction mixture was treated with crushed ice (30 ml), and the solid product was filtered off, dried and recrystallized by hexane.

Figure 14:
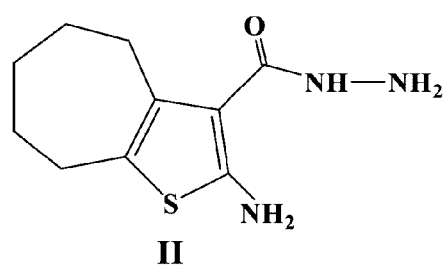
FIG. 14 shows the chemical structure of compound II.

The chemical structure of compound (II) is shown in FIG. 14, was assigned on the basis of the infrared spectra (IR), proton nuclear magnetic resonance spectrum ($^1$H-NMR), carbon nuclear magnetic resonance spectrum ($^{13}$C-NMR), and mass spectrum (MS) spectral data, as shown in FIGS. 15-18, respectively.

Figure 15:
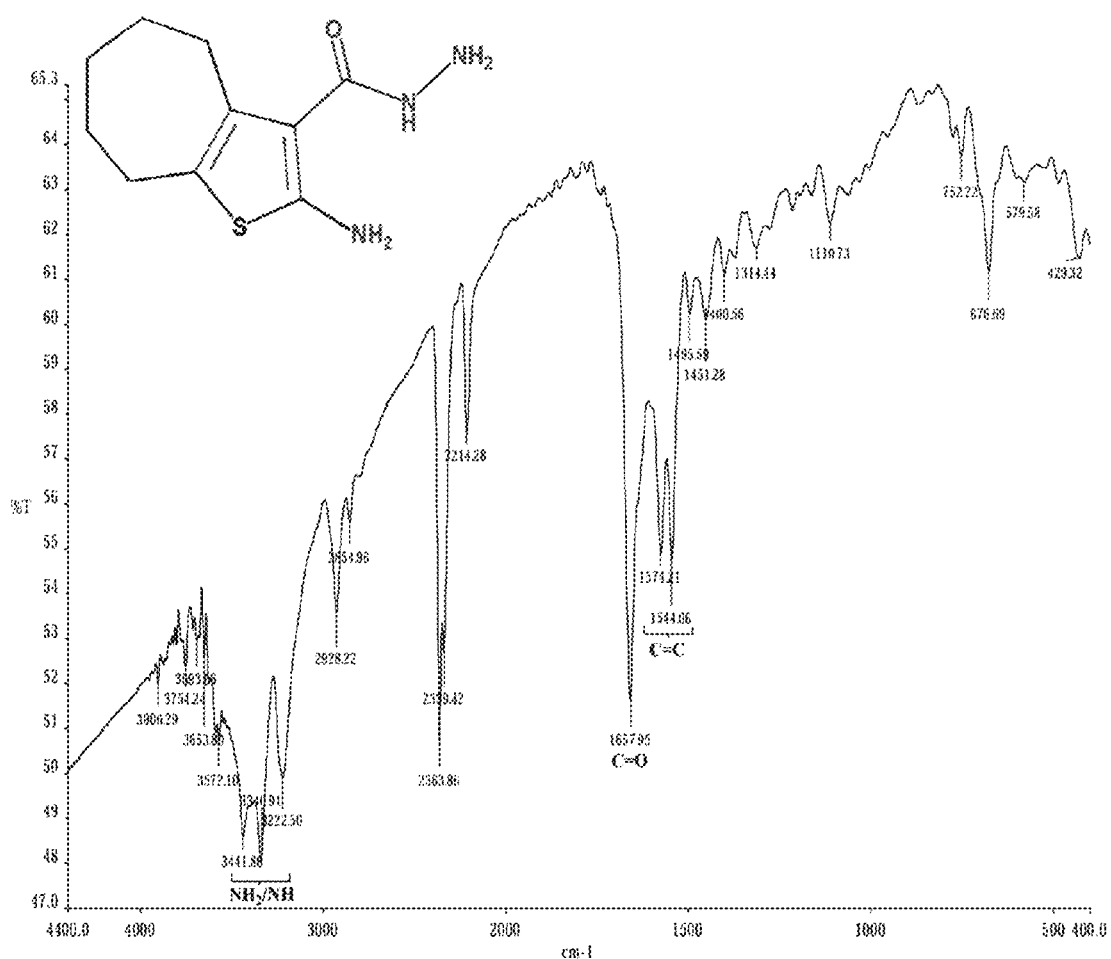
FIG. 15 depicts the infrared spectra of compound II.

The infrared (IR) spectra of compound (II), FIG. 15, showed absorption peaks at 3441.68, 3340.91, 3222.50 cm$^1$ (NH$_2$/NH), 1675.95 cm$^{-1}$ (C=O), 1574.21, 1544.06 cm$^{-1}$ (C=C).

Figure 16:
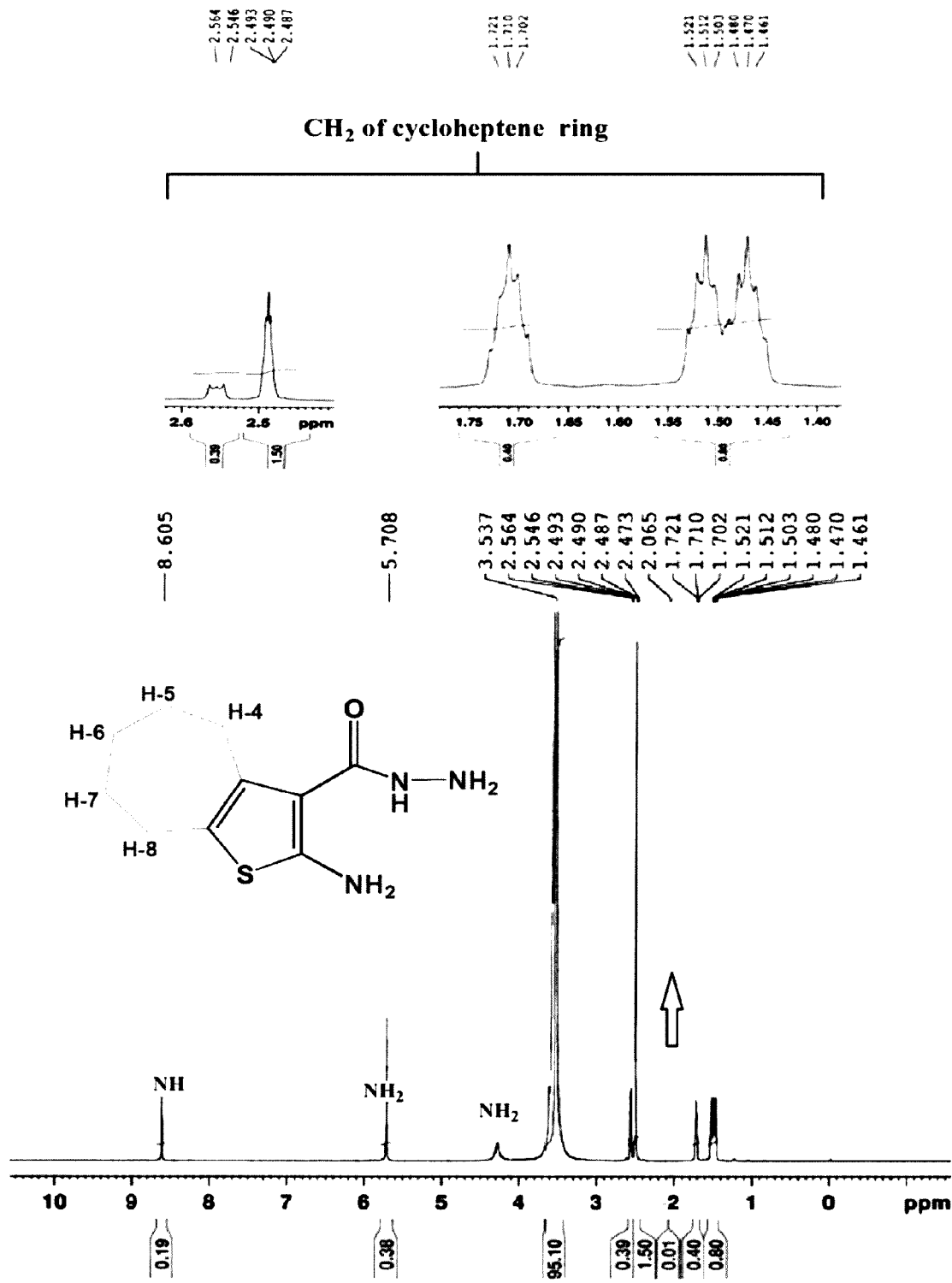
FIG. 16 depicts the nuclear magnetic resonance spectrum of the protons compound II.

The proton nuclear magnetic resonance spectra (H-NMR) of compound (II), FIG. 16, showed a multiplet at δ 1.45-1.53 ppm (4H, H-5,7), a multiplet at δ 1.71 ppm (2H, H-6), a triplet at δ 2.49 ppm (2H, $^3$J=5.4 Hz, H-8), and a triplet at δ 2.56 ppm (2H, $^3$J=5.4 Hz, H-4) corresponding to the methylene groups protons in the cycloheptene moiety, while the NH$_2$ and NH protons appeared as a singles at 4.29 ppm (2H), 5.71 ppm (2H), and 8.61 ppm (1H), respectively.

Figure 17:
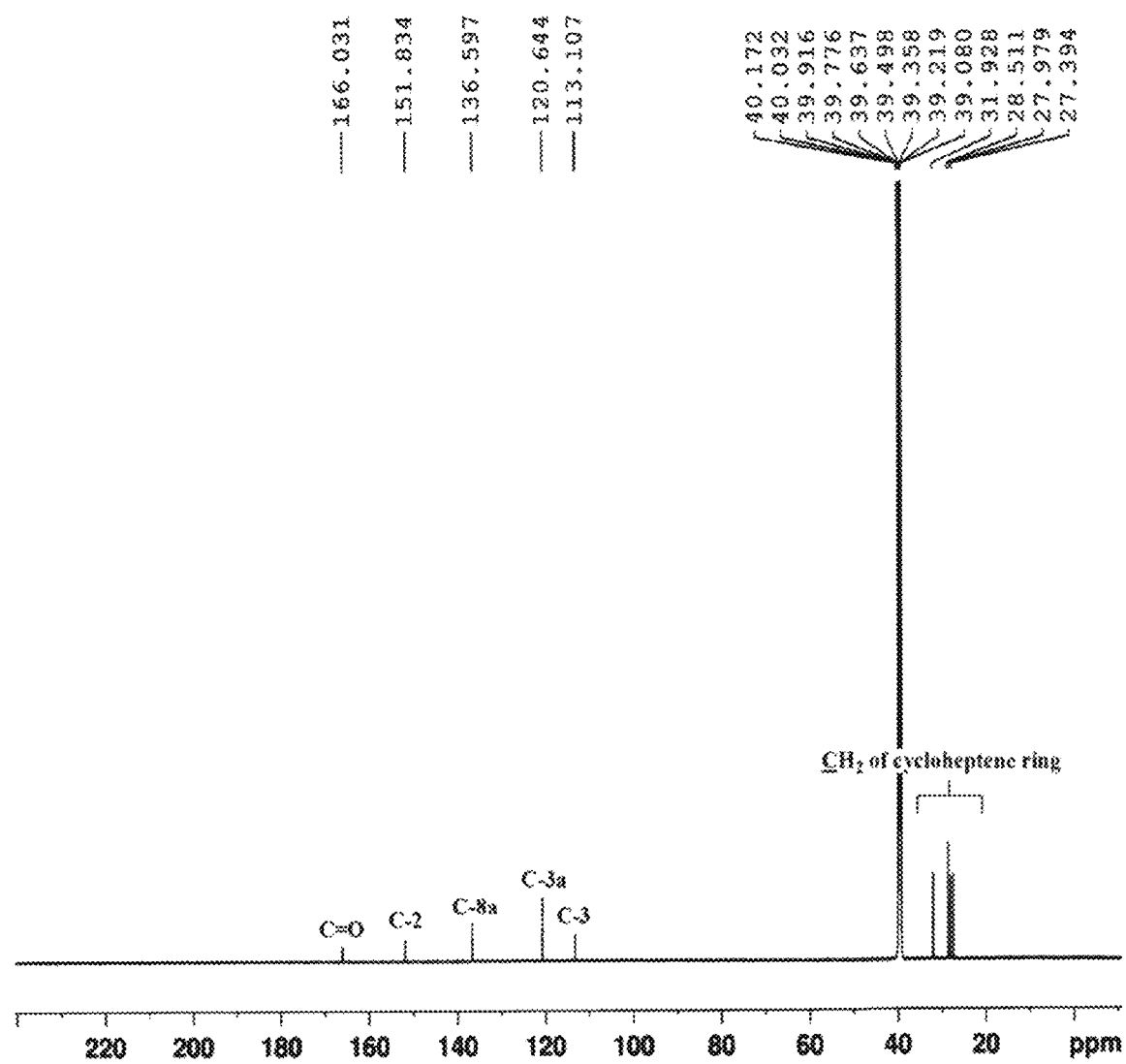
FIG. 17 depicts the nuclear magnetic resonance of the carbons in compound II.

The carbon nuclear magnetic resonance spectra ($^{13}$C-NMR), for compound (II) FIG. 17, showed the cycloheptene ring as four peaks at δ 27.39, 27.98, 28.51, 31.93 ppm (C4-8); the thiophene ring showed as four peaks at δ 113.11 (C-3), 120.64 (C-3a), 136.83 (C-8a), and 151.83 (C-2); and the carbonyl carbon appeared at δ 166.30 ppm.

Figure 18:
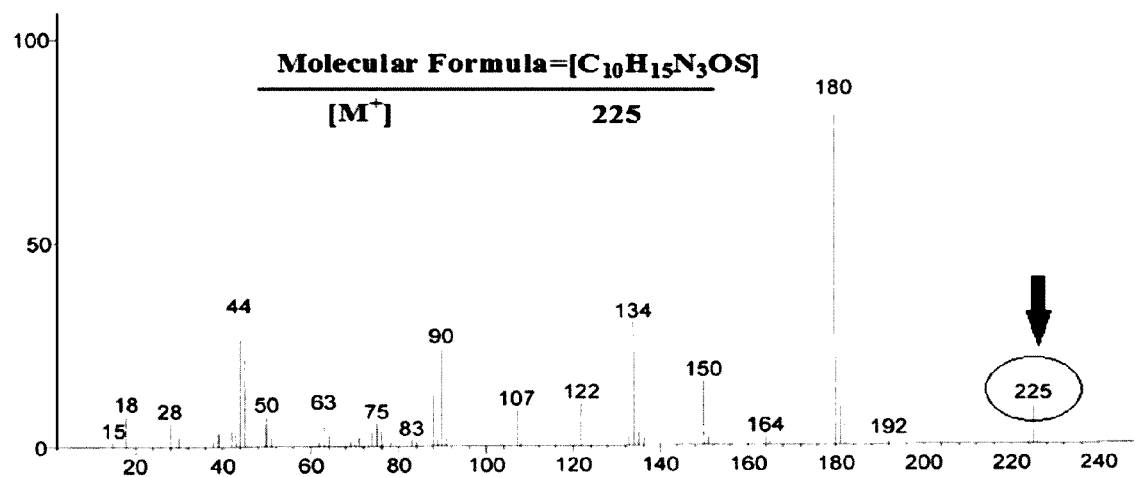
FIG. 18 depicts the mass spectrum of compound II.

The mass spectra (MS) for compound (II), FIG. 18, showed the molecular ion peak at m/z 225 (9.7%); and the fragments, m/z (%): 225 (9.7) [M$^+$], 192 (1.4), 180 (99.9), 150 (15.7), 134 (30.2), 107 (8.8), 90 (24.1), 44 (31.8).

Compound III:

Several methods (methods A, B and C) were used for the preparation of compound (III), the compound of the invention, "2-((4-Nitrophenyl)amino)-6,7,8,9-tetrahydro-3H-cyclohepta[4,5]thieno[2,3-d]pyrimidin-4(5H)-one". Compound II was reacted with 4-nitrophenylisothiocyanate in dry N,N-dimethylformamide (DMF) as solvent by the conventional method (method A), the microwave method (method B), and the ultrasound method (method C) to get the compound of the invention.

In accordance with method A, the conventional method, 4-nitrophenylisothiocyanate (2 mmol) was added to a solution of compound II (0.23 g, 1 mmol) in dry dimethylformamide (DMF) (20 ml) and the mixture as heated under reflux for 8 hours. On cooling, the mixture was poured onto cold water (60 ml) and the separated precipitate was filtered, washed with water, dried and recrystallized by an ethanol/H$_2$O solution.

In accordance with method B, the microwave method, a mixture of compound II (0.23 g, 1 mmol) and 4-nitrophenyl isothiocyanate (2 mmol) in dry dimethylformamide (DMF) (2 ml) was placed in a 50 ml beaker covered with a watch glass and then irradiated with microwaves (520 W) for 2 minutes. On cooling, the mixture was poured onto cold water (10 ml) and the separated precipitate was filtered, washed with water, dried and recrystallized by ethanol/$H_2O$ solution.

In accordance with method C, the ultrasound method, compound II (0.23 g, 1 mmol) was irradiated in dimethylformamide (DMF) (10 ml) and 4-nitro phenylisothiocyanate (2 mmol) by ultrasound for 2 hours. After cooling, water was added (30 ml) and the separated solid was collected by filtration, dried and recrystallized by an ethanol/$H_2O$ solution.

Figure 20:
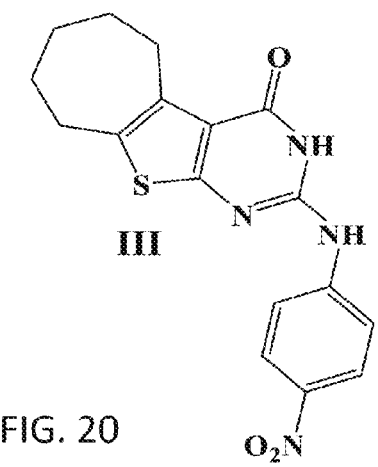
FIG. 20 shows the chemical structure of the compound of the invention.

The chemical structure of compound III, the compound of the invention, shown in FIG. 20, was assigned on the basis of the infrared spectra (IR), proton nuclear magnetic resonance spectrum ($^1$H-NMR), carbon nuclear magnetic resonance spectrum ($^{13}$C-NMR), and mass spectrum (MS) spectral data, as shown in FIGS. 21-24, respectively.

Figure 21:
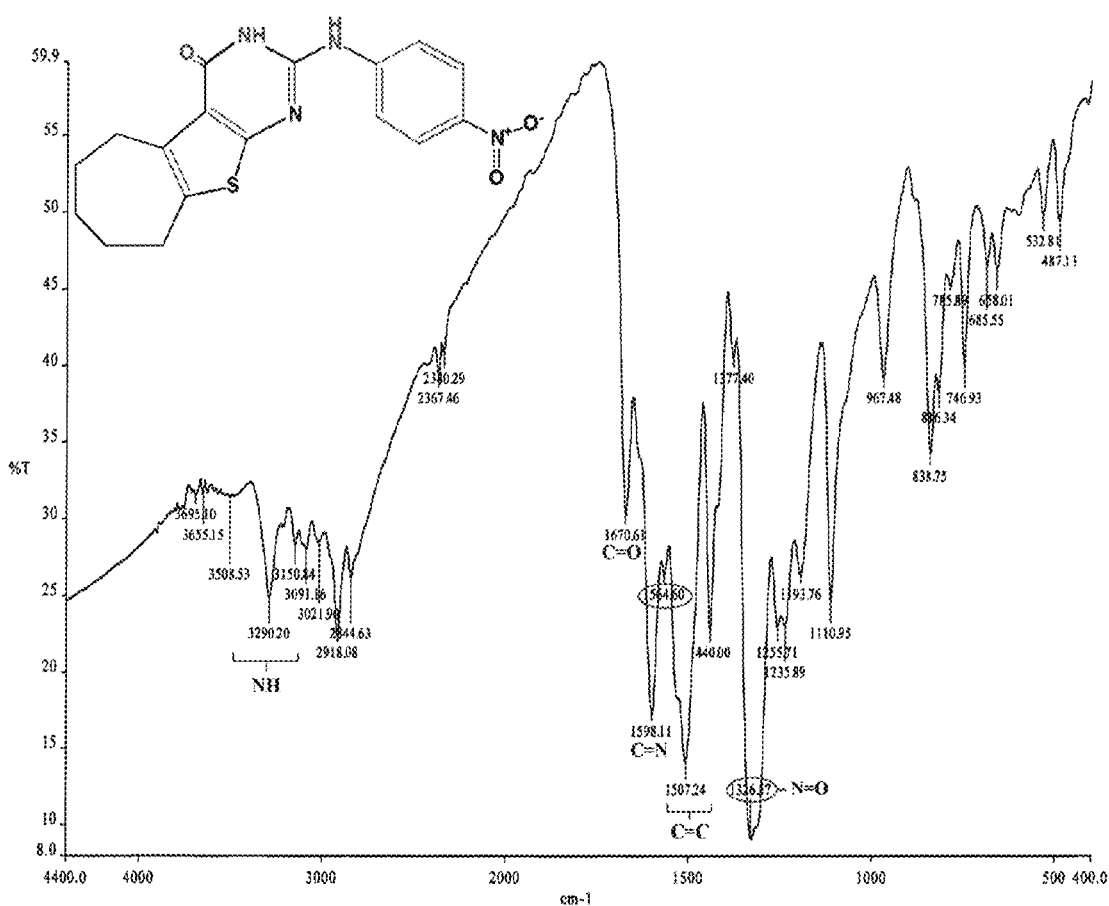
FIG. 21 depicts the infrared spectra of the compound of the invention.

The infrared spectra (IR) for compound III, FIG. 21, showed absorption peaks at 3290.20 cm-1 (2×NH), 1670.61 cm$^{-1}$ (C=O), 1598.11 cm$^{-1}$ (C=N), 1507.24 cm$^{-1}$ (C=C aromatic), 1564.60, 1326.57 cm$^{-1}$ (N=O).

Figure 22:
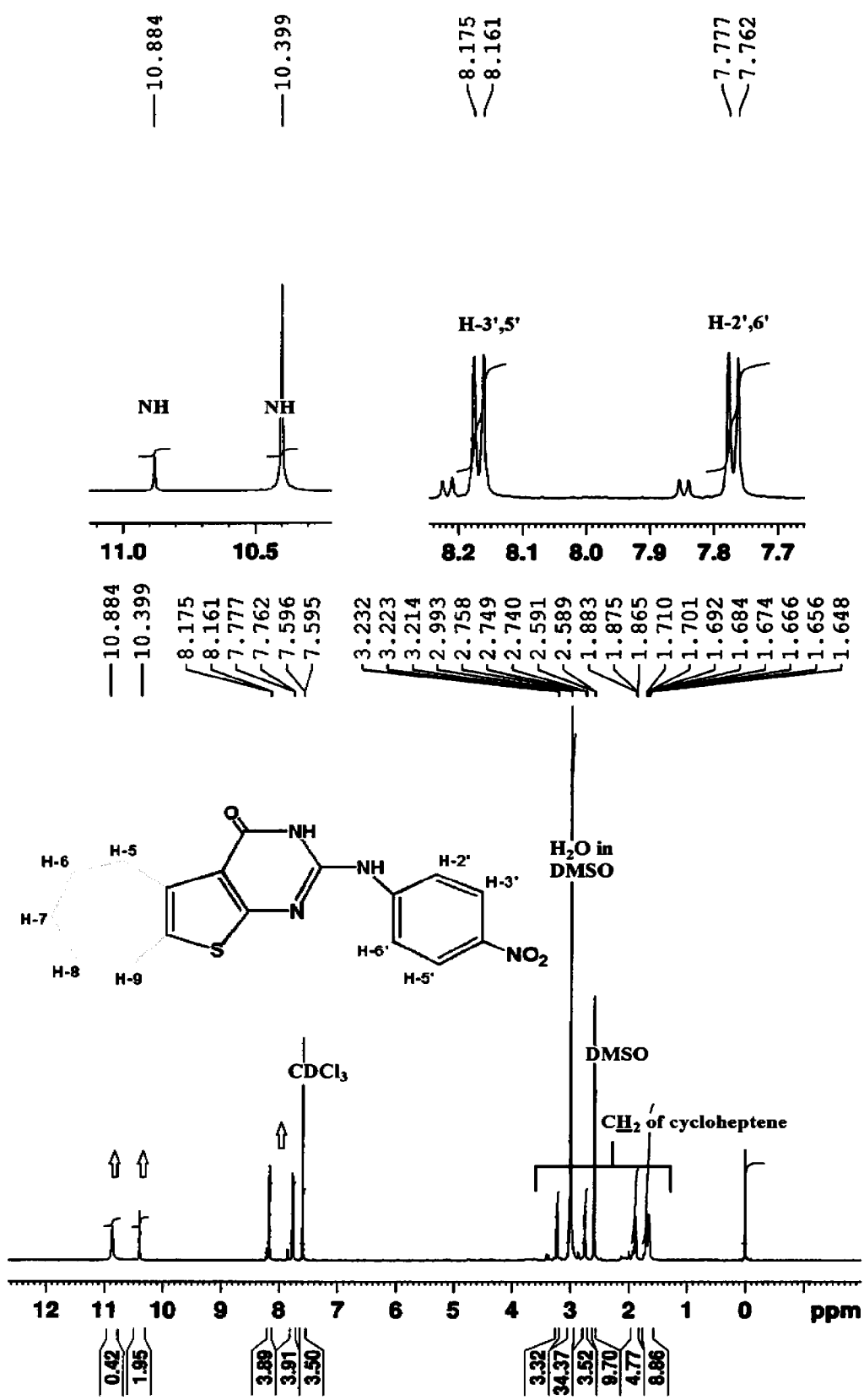
FIG. 22 depicts the nuclear magnetic resonance spectrum of the protons of the compound of the invention.

The proton nuclear magnetic resonance spectra ($^1$H-NMR) for compound III, FIG. 22, are characterized by the presence of cycloheptene protons as a multiplet at δ 1.65 (2H) ppm, 1.69 (2H) ppm (H-6,8), a multiplet at 1.88 ppm (2H, H-7), a triplet at 2.75 ppm (2H, $^3$J=5.4 Hz, H-9), a triplet at 3.22 ppm (2H, $^3$J=5.4 Hz, H-5). In addition to two doublet signals, each integrated two protons at δ 7.77 ppm ($^3$J=8.4 Hz) and at 8.17 ppm ($^3$J=8.4 Hz) due to the protons of the 4 nitro benzene ring (H-2' and H-6') and (H-3' and H-5') respectively. The two NH protons appeared as two singles 10.34, 10.88 ppm, respectively.

Figure 23:
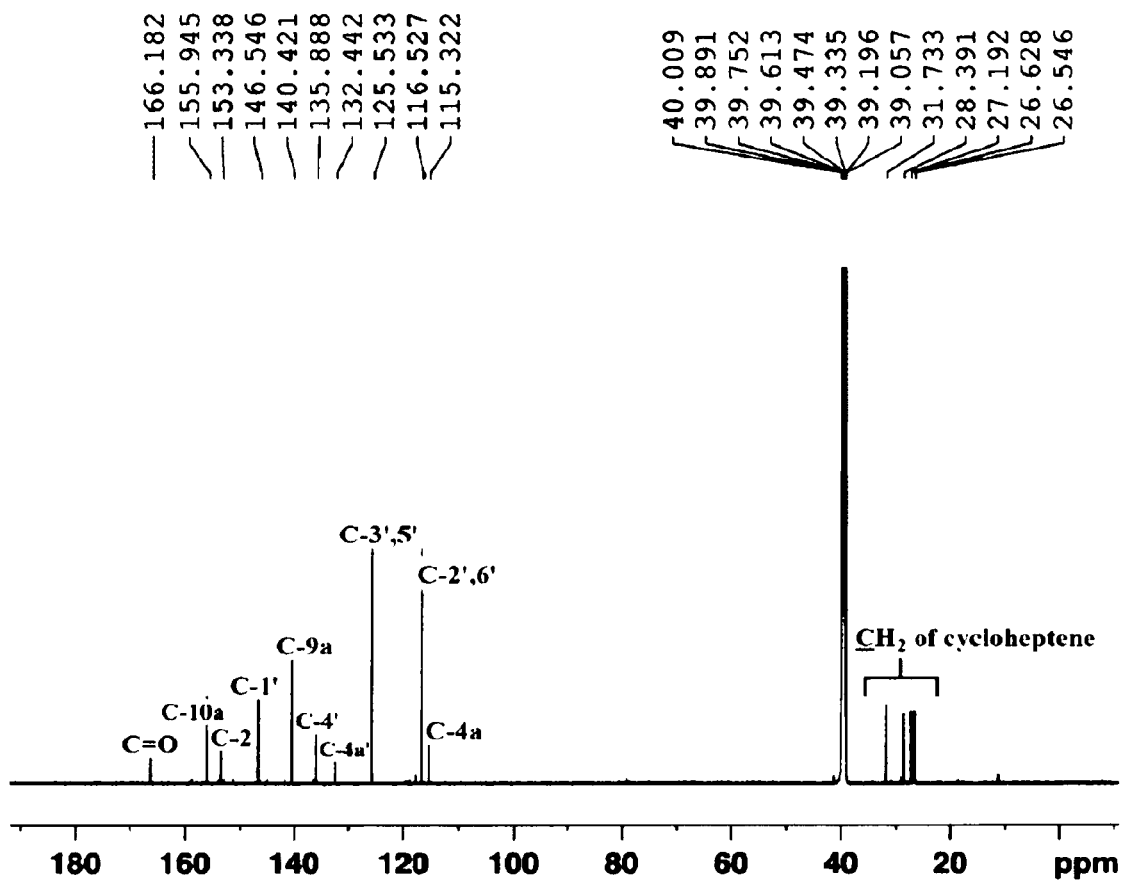
FIG. 23 depicts the nuclear magnetic resonance spectrum of the carbons in the compound of the invention.

The carbon nuclear magnetic resonance spectra ($^{13}$C-NMR) for compound III, FIG. 23, are characterized by the presence of the cycloheptene carbons as five peaks at δ 26.55, 26.63, 27.19, 28.39, 31.73 ppm (C5-9). The assignments of the C-4a, C-4a', C-9a, C-10a and C-2 of the thieno[2,3-d]pyrimidine system appeared at δ 115.32, 132.44, 140.42, 155.95 and 153.34 ppm respectively. The aromatic carbons appeared as four peaks at δ 116.53 ppm (2C, C-2',6'), 125.53 ppm (2C, C-3',5'), 135.89 ppm (1C, C-4'), 146.55 ppm (1C, C-1'), while carbonyl carbon appeared at δ 166.18 ppm.

Figure 24:
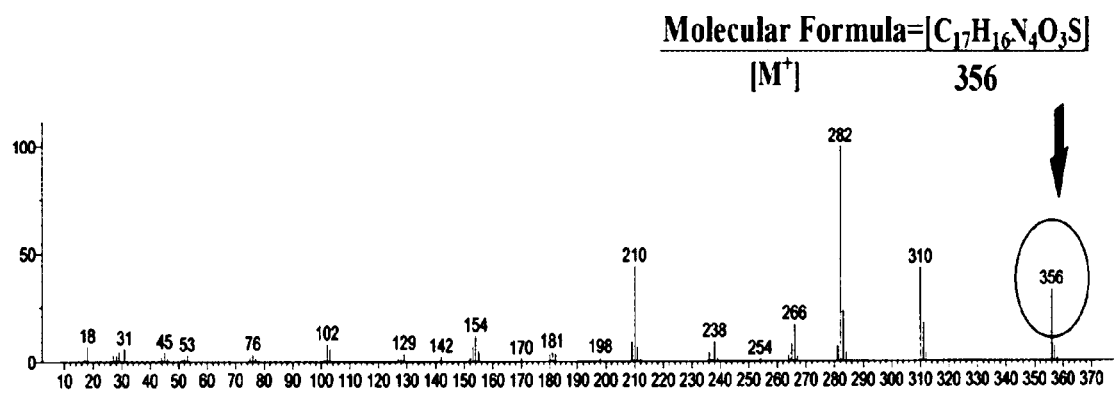
FIG. 24 depicts the mass spectrum of the compound of the invention.

The mass spectra (MS) for compound III, FIG. 24, showed the molecular ion peak at m/z 356 (33.1%). The fragments, m/z (%): 356 (33.1) [M$^+$], 310 (43.3), 282 (99.9), 210 (44.2), 154 (12.1), 102 (8.3), 76 (3.5).

Table 1 shows the physical properties of the above-mentioned compounds.

TABLE 1

| Comp | Mol. Formula | Yield | M.P (° C.) | Solvent of Recrystallization | Color |
|---|---|---|---|---|---|
| I | $C_{12}H_{17}NO_2S$ (239) | 82% | 85 | Petroleum ether 60-80° C. | Orange |
| II | $C_{10}H_{15}N_3OS$ (225) | 53% | 164 | Hexane | White |
| III | $C_{17}H_{16}N_4O_3S$ (356) | 63% | 298 | $H_2O$/Ethanol | Yellow |

Figure 25:
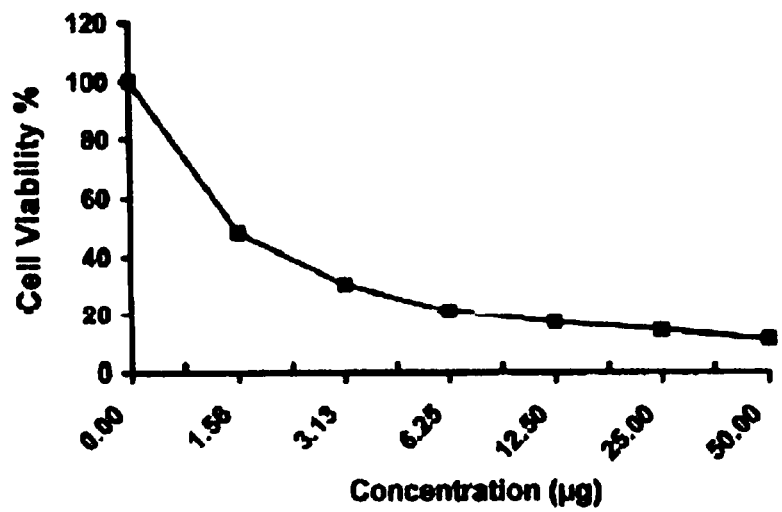
FIG. 25 is a graph of the cytotoxicity of Doxorubicin against HepG2.
Figure 26:
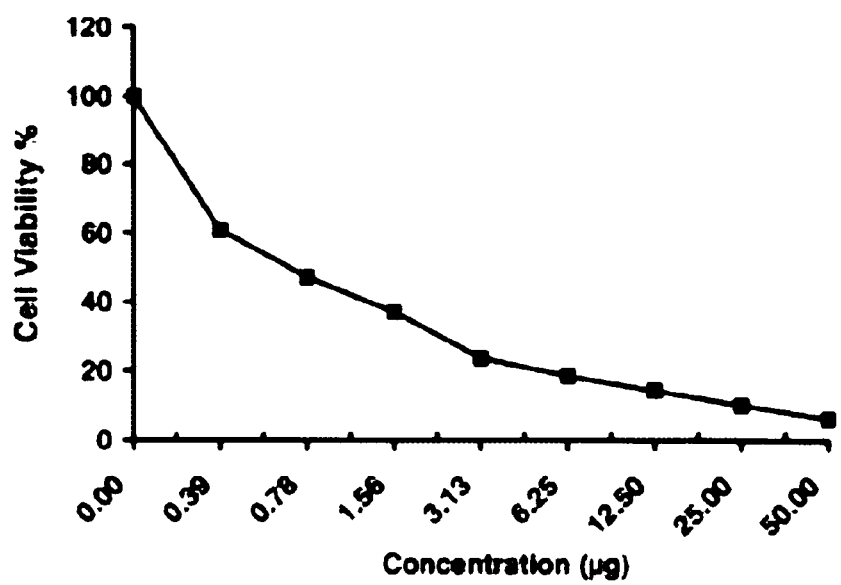
FIG. 26 is a graph of the cytotoxicity of the chemical compound of the invention against HepG2.

Evaluation of the cytotoxicity of the Doxorubicin standard and the compound of the invention against the HepG2 cell line are shown in FIGS. 25 and 26 and in tables 2 and 3.

HepG2 cells (human cell line of a well differentiated hepatocellular carcinoma isolated from a liver biopsy of a male Caucasian aged 15 years) were obtained from the American Type Culture Collection (ATCC). The chemicals used were: Dimethyl sulfoxide (DMSO), crystal violet and trypan blue dye, purchased from Sigma, St. Louis, Mo., USA; DMEM, RPMI-1640, FBS, HEPES buffer solution, L-glutamine, gentamycin and 0.25% Trypsin-EDTA, purchased from BioWhittaker®, Lonza, Belgium; and Crystal violet stain (1%), composed of 0.5% (w/v) crystal violet and 50% methanol, made up to volume with ddH20 and filtered through a Whatmann No. I filter paper.

In the cytotoxicity assay, the cells were propagated in Dulbecco's modified Eagle's medium (DMEM) supplemented with 10% heat-inactivated fetal bovine serum, 1% L-glutamine, HEPES buffer and 50 µg/ml gentamycin. All cells were maintained at 37° C. in a humidified atmosphere with 5% $CO_2$ and were subcultured two times a week.

Cell toxicity was monitored by determining the effect of the test samples on cell morphology and cell viability.

Cytotoxicity Evaluation Using Viability Assay:

For cytotoxicity assay, the cells were seeded in a 96-well plate at a cell concentration of $1 \times 10^4$ cells per well in 100 µl of growth medium. Fresh medium containing different concentrations of the test sample was added after 24 hours following seeding. Serial two-fold dilutions of the tested chemical compound were added to confluent cell monolayers dispensed into 96-well, flat-bottomed microtiter plates (Falcon, N.J., USA) using a multichannel pipette. The microtiter plates were incubated at 37° C. in a humidified incubator with 5% $CO_2$ for a period of 48 hours. Three wells were used for each concentration of the test sample. Control cells were incubated without test sample and with or without DMSO. The little percentage of DMSO present in the wells (maximal 0.1%) was found not to affect the experiment. After incubation of the cells for 24 hours at 37° C., various concentrations of sample (50, 25, 12.5, 6.25, 3.125 & 1.56 µg) were added, and the incubation was continued for 48 hours and viable cells yield was determined by a colorimetric method.

In brief, after the end of the incubation period, media were aspirated and the crystal violet solution (1%) was added to each well for at least 30 minutes. The stain was removed and the plates were rinsed using tap water until all excess stain was removed. Glacial acetic acid (30%) was then added to all wells and mixed thoroughly and then the absorbance of the plates was measured after being gently shaken on a Microplate reader (TECAN, Inc.), using a test wavelength of 490 nm. All results were corrected for background absorbance detected in wells without added stain. Treated samples were compared with the cell control in the absence of the tested compound. All experiments were carried out in triplicate.

The cell cytotoxic effect of tested compound was calculated according to the rapid colorimetric assay for cellular growth and survival: application to proliferation and cytotoxicity assay, published by T. Mosmann in the Journal of Immunology Methods, 1983, 65:55-63; and the antiviral activity of medicinal plants of Nilgriris, published by P. Vijayan et al. in the Indian Journal of Medical Research, 2004, 120: 24-29.

FIG. 25 and table 2 highlight the effectiveness of the reference compound (Doxorubicin) as an inhibitor to the growth and proliferation of liver cancer cells (HepG2) at different concentration degrees.

TABLE 2

| Sample conc. (μg) | Viability % |
|---|---|
| 50 | 10.95 |
| 25 | 14.29 |
| 12.5 | 16.90 |
| 6.25 | 21.03 |
| 3.125 | 30.32 |
| 1.56 | 48.25 |
| 0.78 | 57.44 |
| 0 | 100.00 |

As illustrated in FIG. 25 and Table 2, the inhibitory activity of doxorubicin standard against HepG2 (Hepatocellular carcinoma cells) as detected under the experimental conditions of the invention showed $IC_{50}=1.2$ μg.

FIG. 26 and table 3 highlight the effectiveness of the compound of the invention, "2-((4-Nitrophenyl)amino)-6,7,8,9-tetrahydro-3H-cyclohepta[4,5]thieno[2,3-d]pyrimidin-4(5H)-one" as an inhibitor to the growth and proliferation of liver cancer-cells (HepG2) at different concentration degrees.

TABLE 3

| Sample conc. (μg) | Viability % | |
|---|---|---|
| 50 | 6.32 | ✧ |
| 25 | 10.21 | ✧ |
| 12.5 | 14.37 | ✧ |
| 6.25 | 18.54 | ✧ |
| 3.125 | 23.73 | ✧ |
| 1.56 | 36.92 | ✧ |
| 0.78 | 47.14 | ✧ |
| 0.39 | 60.76 | |
| 0 | 100.00 | |

As illustrated in FIG. 26 and Table 3, the inhibitory activity of the compound of the invention against HepG2 (Hepatocellular carcinoma cells) as detected under the experimental conditions of the invention showed $IC_{50}=0.7$ μg.

While particular embodiments of the invention have been illustrated and described in detail herein, it should be understood that various changes and modifications may be made in the invention without departing from the spirit and intent of the invention as defined by the appended claims.

What is claimed is:

1. A chemical compound for inhibiting the growth and proliferation of human liver cancer cells (HepG2), said compound consisting of 2-((4-nitrophenyl)amino)-6,7,8,9-tetrahydro-3H-cyclohepta[4,5]thieno[2,3-d]pyrimidin-4(5H)-one, said compound also being represented as follows:

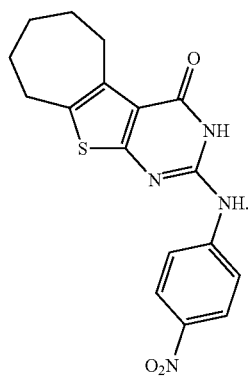 [SMILES: O=c1[nH]c(Nc2ccc([N+](=O)[O-])cc2)nc2sc3c(c12)CCCCC3]

2. A method of synthesizing an effective chemical compound that inhibits the growth and proliferation of human liver cancer cells HepG2, comprising the steps of:
preparing a first chemical compound expressed by the formula ethyl-2-amino-5,6,7,8-tetrahydro-4H-cyclohepta[b]thiophene-3-carboxylate;
preparing a second chemical compound expressed by the formula 2 amino-5,6,7,8-tetrahydro-4H-cyclohepta[b]thiophene-3-carbohydrazide, by reaction of the first chemical compound with excess of hydrazine hydrate in absolute ethanol as solvent; and
preparing the effective chemical compound of the invention by reaction of the second chemical compound with 4-nitrophenylisothiocyanate in dry dimethylformamide as solvent, wherein the compound of the invention has the chemical formula 2-((4-nitrophenyl)amino)-6,7,8,9-tetrahydro-3H-cyclohepta[4,5]thieno[2,3-d]pyrimidin-4(5H)-one.

3. The method as claimed in claim 2, wherein:
during preparation of the second chemical compound, the first chemical compound was added in the amount of 0.24 g, 1 mmol, the hydrazine hydrate was added in the amount of 5 mmol, the absolute ethanol was added in the amount of 20 ml to form a mixture, the mixture was refluxed for 18 hours to produce a reaction mixture and then cooled; and
following cooling, the reaction mixture was treated with 50 ml of crushed ice, and resulting solid product was filtered off and recrystallized by hexane.

4. The method as claimed in claim 2, wherein:
during preparation of the second chemical compound, the first chemical compound was added in the amount of 0.24 g, 1 mmol, the hydrazine hydrate was added in the amount of 1 ml, the absolute ethanol solvent was added in the amount of 2 drops to form a mixture, the mixture was placed in a 50 ml beaker covered with a watch glass and then exposed to 390 watts of microwave radiation for 30 minutes to produce a reaction mixture and then cooled; and
following cooling, the reaction mixture was treated with 20 ml of crushed ice and resulting solid product was filtered off and recrystallized by hexane.

5. The method as claimed in claim 2, wherein:
during preparation of the second chemical compound, the first chemical compound was added to the mixture in the amount of 0.24 g, 1 mmol, the hydrazine hydrate was added in the amount of 5 mmol, the absolute ethanol was added in the amount of 10 ml to form a mixture, the mixture was subjected to ultrasound radiation for 4 hours to form a reaction mixture and then cooled; and
after cooling, the reaction mixture was treated with 30 ml of crushed ice, and resulting solid product was filtered off and recrystallized by hexane.

6. The method as claimed in claim 3, wherein:
during preparation of the effective chemical compound of the invention, the second chemical compound was added in the amount of 0.23 g, 1 mmol, the 4-nitrophenylisothiocyanate was added in the amount of 2 mmol, the dry dimethylformamide (DMF) was added in the amount of 20 ml to form a mixture, the mixture was heated under reflux for 8 hours to form a reaction mixture and then cooled; and
after cooling, the reaction mixture was poured onto 60 ml of cold water to separate precipitate and the separated precipitate was filtered, washed with water, dried and recrystallized by an ethanol/$H_2O$ solution.

7. The method as claimed in claim 3, wherein:
during preparation of the effective chemical compound of the invention, the second chemical compound was added in the amount 0.23 g, 1 mmol, the 4-nitrophenylisothiocyanate was added in the amount of 2 mmol, and 2 ml of the dry dimethylformamide (DMF) was added to form a mixture, the mixture was placed in a 50 ml beaker covered with a watch glass and irradiated with 520 W of microwave energy for 2 minutes to form a reaction mixture; and
after cooling, the reaction mixture was poured onto 10 ml of cold water to separate precipitate, and separated precipitate was filtered, washed with water, dried and recrystallized by an ethanol/$H_2O$ solution.

8. The method as claimed in claim 3, wherein:
during preparation of the effective chemical compound of the invention, the second chemical compound was added to the mixture in the amount of 0.23 g, 1 mmol, the 4 nitrophenylisothiocyanate was added in the amount of 2 mmol, and the dry dimethylformamide (DMF) was added in the amount of 10 ml to form a mixture, the mixture was subjected to ultrasound radiation for 2 hours to form a reaction mixture and then cooled; and
after cooling, the reaction mixture was poured onto 30 ml of cold water to separate precipitate, and the separated precipitate was filtered, washed with water, dried and recrystallized by an ethanol/$H_2O$ solution.

9. The method as claimed in claim 4, wherein:
during preparation of the effective chemical compound of the invention, the second chemical compound was added in the amount of 0.23 g, 1 mmol, the 4-nitrophenylisothiocyanate was added in the amount of 2 mmol, the dry dimethylformamide (DMF) was added in the amount of 20 ml to form a mixture and the mixture was heated under reflex for 8 hours to form a reaction mixture and then cooled; and
after cooling, the reaction mixture was poured onto 60 ml of cold water to separate precipitate and the separated precipitate was filtered, washed with water, dried and recrystallized by ethanol/$H_2O$ solution.

10. The method as claimed in claim 4, wherein:
during preparation of the effective chemical compound of the invention, the second chemical compound was added in the amount 0.23 g, 1 mmol, the 4-nitrophenylisothiocyanate was added in the amount of 2 mmol, and 2 ml of the dry dimethyl dimethylformamide (DMF) was added to form a mixture, the mixture was placed in a 50 ml beaker covered with a watch glass and irradiated with 520 W of microwave energy for 2 minutes to form a reaction mixture and then cooled; and
after cooling, the reaction mixture was poured onto 10 ml of cold water to separate precipitate, and separated precipitate was filtered, washed with water, dried and recrystallized by an ethanol/$H_2O$ solution.

11. The method as claimed in claim 4, wherein:
during preparation of the effective chemical compound of the invention, the second chemical compound was added to the mixture in the amount of 0.23 g, 1 mmol, the 4 nitrophenylisothiocyanate was added in the amount of 2 mmol, and the dry dimethylformamide (DMF) was added in the amount of 10 ml to form a mixture, the mixture was subjected to ultrasound radiation for 2 hours to form a reaction mixture and then cooled; and
after cooling, the reaction mixture was poured onto 30 ml of cold water to separate precipitate, and separated precipitate was filtered, washed with water, dried and recrystallized by an ethanol/$H_2O$ solution.

12. The method as claimed in claim 5, wherein:
during preparation of the effective chemical compound of the invention, the second chemical compound was added in the amount of 0.23 g, 1 mmol, the 4-nitrophenylisothiocyanate was added in the amount of 2 mmol, the dry dimethylformamide (DMF) was added in the amount of 20 ml to form a mixture, the mixture was heated under reflex for 8 hours to form a reaction mixture and cooled; and
after cooling, the reaction mixture was poured onto 60 ml of cold water to separate precipitate and the separated precipitate was filtered, washed with water, dried and recrystallized by ethanol/$H_2O$ solution.

13. The method as claimed in claim 5, wherein:
during preparation of the effective chemical compound of the invention, the second chemical compound was added in the amount 0.23 g, 1 mmol, the 4-nitrophenylisothiocyanate was added in the amount of 2 mmol, and 2 ml of the dry dimethyl dimethylformamide (DMF) was added to form a mixture, the mixture was placed in a 50 ml beaker covered with a watch glass and irradiated with 520 W of microwave energy for 2 minutes to form a reaction mixture and then cooled; and
after cooling, the reaction mixture was poured onto 10 ml of cold water to separate precipitate, and the separated precipitate was filtered, washed with water, dried and recrystallized by an ethanol/$H_2O$ solution.

14. The method as claimed in claim 5, wherein:
during preparation of the effective chemical compound of the invention, the second chemical compound was added to the mixture in the amount of 0.23 g, 1 mmol, the 4 nitrophenylisothiocyanate was added in the amount of 2 mmol, and the dry dimethylformamide (DMF) was added in the amount of 10 ml to form a mixture, the mixture was subjected to ultrasound radiation for 2 hours to form a reaction mixture and then cooled; and
after cooling, the reaction mixture was poured onto 30 ml of cold water to separate precipitate, and separated precipitate was filtered, washed with water, dried and recrystallized by an ethanol/$H_2O$ solution.

15. The method as claimed in claim 2, wherein:
the first chemical compound is prepared by mixing and stirring together the ingredients cycloheptanone, ethyl cyanoacetate, sulfur and ethanol and adding the chemical diethylamine until the sulfur is dissolved, followed by stirring the mixture cold overnight, and then treating the reaction mixture with crushed ice, filtering off solid product, and drying and recrystallizing the solid product with petroleum ether.

16. The method as claimed in claim 15, wherein:
during preparation of the first chemical compound the cycloheptanone is added in the amount of 5.60 g, 0.05 mmol, the ethyl cyanoacetate is added in the amount of 5.65 g, 0.05 mmol, the sulfur is added in the amount of 1.67 g, the ethanol is added in the amount of 10 ml, 10 ml of the diethylamine is added dropwise until the sulfur is dissolved, 60 ml of crushed ice is used to treat the reaction mixture, and 60-80% petroleum ether is used to recrystallize the solid product.

17. A method of synthesizing a chemical compound that is effective to inhibit the growth and proliferation of human liver cancer cells HepG2, comprising the steps of:

preparing a first compound by a reaction mixture of cycloheptanone, ethyl cyanoacetate, sulfur, ethanol and diethylamine, wherein the first compound is expressed by the formula ethyl-2-amino-5,6,7,8-tetrahydro-4H-cyclohepta[b]thiophene-3-carboxylate;

preparing a second compound by heating the first compound with excess of hydrazine hydrate in absolute ethanol as solvent, wherein the second compound is expressed by the formula 2-amino-5,6,7,8-tetrahydro-4H-cyclohepta[b]thiophene-3-carbohydrazide; and reacting the second compound with 4-nitrophenylisothiocyanate in dry dimethylformamide (DMF) as solvent to produce the chemical compound that is effective to inhibit the growth and proliferation of human liver cancer cells HepG2, said compound being expressed by the formula 2-((4-nitrophenyl)amino)-6,7,8,9-tetrahydro-3H-cyclohepta[4,5]thieno[2,3-d]pyrimidin-4(5H)-one.

* * * * *

UNITED STATES PATENT AND TRADEMARK OFFICE
CERTIFICATE OF CORRECTION

PATENT NO. : 9,487,540 B2
APPLICATION NO. : 14/668837
DATED : November 8, 2016
INVENTOR(S) : Zainab Saeed Alghamdi It is certified that error appears in the above-identified patent and that said Letters Patent is hereby corrected as shown below:

In the Abstract:
Line 2, "thieno-[2,3-d]pyrimidin" should read --thieno[2,3-d]pyrimidin--.

Column 2:
Line 28, that portion of the chemical name reading "*tetrahydro[1]benzothieno*" should read --*tetrahydro[1]benzothieno*--;
Lines 37 and 38, "2004; 13; 347. 2004; 13; 347" should read --2004; 13; 347--.
Lines 41 and 42, "(1,3,4) thiadiazole(2,3-b)tetrahydro-benzothieno[3,2-e]pyrimidines" should read --(1,3,4)thiadiazole(2,3-b)tetrahydrobenzothieno[3,2-e]pyrimidines--.

Column 6:
Line 22, "3222.50 cm-1" should read --3222.50 cm$^{-1}$--;
Line 25, "H-NMR" should read --$^{1}$H-NMR--.

Column 7:
Line 6, "4-nitro phenylisothiocyanate" should read --4-nitrophenylisothiocyanate--;
Line 18, "3290.20 cm-1" should read --3290.20 cm$^{-1}$--.

Column 10:
Lines 8 and 9, "2 amino-5,6,7,8-tetrahydro-4*H*-cyclohepta[*b*]thiophene-3-carbohydrazide" should read --2-amino-5,6,7,8-tetrahydro-4*H*-cyclohepta[*b*]thiophene-3-carbohydrazide--.

Column 11:
Line 19, "4 nitrophenylisothiocyanate" should read --4-nitrophenylisothiocyanate--;
Line 47, "dimethyl dimethylformamide" should read --dimethylformamide--;
Line 61, "4 nitrophenylisothiocyanate" should read --4-nitrophenylisothiocyanate--.

Signed and Sealed this
Fourth Day of April, 2017

Michelle K. Lee
*Director of the United States Patent and Trademark Office*

Column 12:
Line 23, "dimethyl dimethylformamide" should read --dimethylformamide--;
Line 37, "4 nitrophenylisothiocyanate" should read --4-nitrophenylisothiocyanate--.